US007364571B2

(12) United States Patent
Schinazi et al.

(10) Patent No.: US 7,364,571 B2
(45) **Date of Patent: *Apr. 29, 2008**

(54) FLOW RESTRICTOR DEVICE FOR A MEDICAL APPARATUS

(76) Inventors: Robert G. Schinazi, 320 Pomelo Dr., Apt. 216, Vista, CA (US) 92081; Lauren E. de Rosset, 320 Pomelo Dr., Apt. 216, Vista, CA (US) 92081

(*) Notice: Subject to any disclaimer, the term of this patent is extended or adjusted under 35 U.S.C. 154(b) by 150 days.

This patent is subject to a terminal disclaimer.

(21) Appl. No.: 10/791,682

(22) Filed: Mar. 2, 2004

(65) Prior Publication Data

US 2005/0197631 A1 Sep. 8, 2005

(51) Int. Cl.
*A61M 5/00* (2006.01)

(52) U.S. Cl. ...................................................... 604/246

(58) Field of Classification Search ........ 604/246–247, 604/523, 251–262, 537, 890.1, 30, 118, 80, 604/81, 126; 138/40–46

See application file for complete search history.

(56) References Cited

U.S. PATENT DOCUMENTS 2,878,836 A * 3/1959 Binks .......................... 138/45
3,868,973 A * 3/1975 Bierman et al. .............. 138/43
4,022,384 A 5/1977 Hoyle et al.
4,200,119 A 4/1980 Cunningham
4,411,292 A 10/1983 Schiller
4,589,872 A 5/1986 Bellin et al.
4,639,019 A 1/1987 Mittleman
4,796,660 A 1/1989 Bron
5,032,264 A 7/1991 Geiger
5,156,680 A 10/1992 Orzechowski
5,549,583 A 8/1996 Sanford
5,609,303 A 3/1997 Cohen
6,497,685 B1 12/2002 Dennehey et al.
6,550,956 B1 * 4/2003 Utracki et al. ........... 366/176.2
6,569,125 B2 5/2003 Jepson et al.
6,569,128 B1 5/2003 Christensen et al.
6,981,967 B2 * 1/2006 Massengale et al. ........ 604/174

OTHER PUBLICATIONS

PCT Search Report, Dec. 7, 2005.

* cited by examiner

*Primary Examiner*—Nicholas Lucchesi
*Assistant Examiner*—Theodore J Stigell
(74) *Attorney, Agent, or Firm*—Dority & Manning

(57) ABSTRACT

A medical apparatus flow restrictor includes a housing having an inlet and an outlet, and a fluid path defined through the housing between the inlet and the outlet. At least one pair of opposed restriction devices are seated within the housing between the inlet and outlet. The restriction devices have opposed surfaces placed in contact against each other and are disposed in the flow path such that fluid delivered through the inlet passes between the opposing surfaces prior to flowing from the outlet. The opposing surfaces have a relative degree of surface roughness and opposed surface area defined as a function of a desired flow rate of fluid through the restrictor.

22 Claims, 7 Drawing Sheets

FIG. 3A
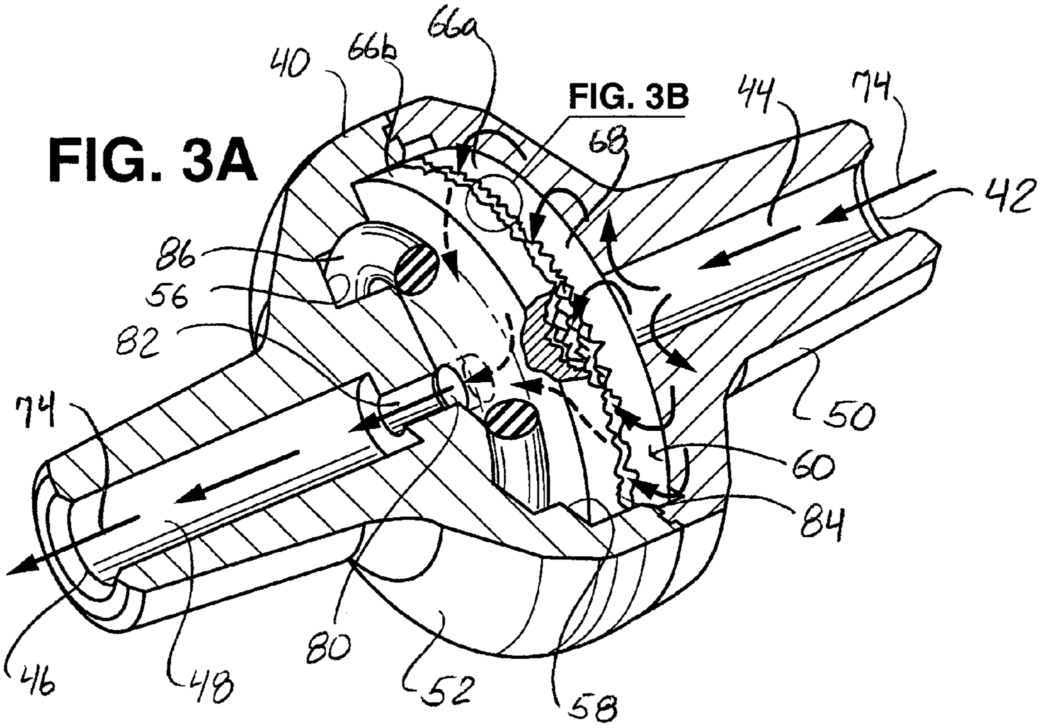
FIG. 3B
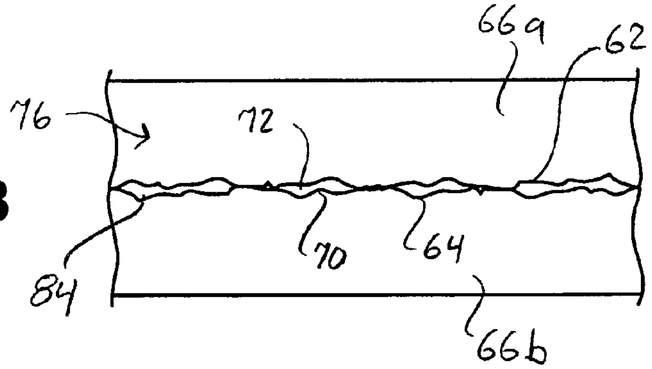
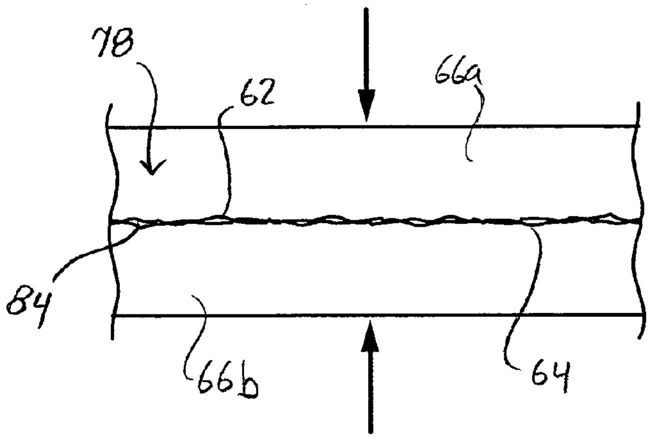
FIG. 3C

FLOW RESTRICTOR DEVICE FOR A MEDICAL APPARATUS

FIELD OF THE INVENTION

The present invention relates generally to the field of flow restriction devices, and more specifically to a flow restrictor that is particularly well suited for regulating the flow of fluids in various medical devices and systems.

BACKGROUND OF THE INVENTION

There are various applications of flow restriction devices in the medical arts for closely regulating the flow of a fluid. One common use of such devices is with an infusion pump system wherein fluid medicine or other fluids are delivered to an injection site on the patient from the infusion pump. Embodiments are known wherein the flow restrictor is contained within the pump body. For example, U.S. Pat. No. 4,386,929 describes a short capillary tube contained within the pump housing for regulating the flow of dispensed medication. It is also known to include a flow restrictor downstream of the infusion pump, for example as with the delivery tube system described in U.S. Pat. No. 4,741,733.

U.S. Pat. No. 6,569,128 describes a catheter flow restriction system wherein a capillary-like restriction tube is contained within a catheter tube. The flow rate through the system is adjusted by trimming the length of the restriction tube and concentric catheter tube. The catheter can then be attached to an infusion device by a suitable connector, such as a Touhy-Borst connector.

Conventional flow restriction devices are, however, not without certain drawbacks, particularly the capillary tube restrictors. For example, such tube-type devices are relatively difficult and expensive to manufacture. Also, as requirements in the medical field tend towards decreased flow rates, it has become increasingly difficult to manufacture the tubes to achieve a specified flow rate due simply to machining tolerances and material limitations. For example, the smaller (in diameter) the tubes become, the more prone they become to particulate clogging.

A need thus exists in the medical field for a more reliable yet inexpensive flow restrictor that may be used in various systems, such as infusions systems and like devices.

SUMMARY OF THE INVENTION

Objects and advantages of the invention will be set forth in part in the following description, or may be obvious from the description, or may be learned through practice of the invention.

In accordance with the invention, a flow restrictor device is provided that is relatively inexpensive to manufacture and assemble, yet will reliably maintain a precisely regulated flow rate. The device is not prone to clogging, and is easily incorporated into any conventional medical infusion or other type of fluid delivery system. In this regard, it should be appreciated that although the inventive restrictor has particular usefulness in an infusion delivery system, the invention is not limited to this particular application. The inventive restrictor may be used in any system wherein it is desired to restrict or regulate the flow of a fluid, and all such uses are within the scope and spirit of the invention.

The term "fluid" is used herein to refer to a gas, liquid, or combination of a gas and liquid.

The flow restrictor according to the invention includes a housing having an inlet and an outlet, and a fluid path defined through the housing between the inlet and outlet. The inlet and outlet are configured to be connected in-line, for example with tubing or the like, in a medical apparatus, such as an infusion system. The inlet and outlet may be releasably connected to the medical apparatus tubing, for example with a simple press fit, clamp, or fitting, or permanently attached by, for example, by way of an adhesive, ultrasonic bond, a weld, and so forth.

At least one pair of opposed restriction devices are seated within the housing between the inlet and outlet. The restriction devices have opposing surfaces placed in contact against each other and are disposed in the flow path such that fluid delivered to the inlet must pass between the opposing surfaces prior to flowing from the outlet. Any one or combination of seals, such as O-rings, gaskets, or the like, may be used within the housing to establish the desired flow path through the devices. A resilient member, such as a spring, wave spring, or similar device may be used to bias the restriction devices together. Alternatively, the seal may be resilient and also function to bias the restriction devices together.

The opposing surfaces of the restriction devices have a relative degree of surface roughness and opposed surface area that are predetermined as a function of a desired flow rate of fluid through the restrictor. Thus, the restrictive flow path between the opposed surfaces of the restriction devices has a metering or restrictive effect on the rate of flow through the device, as described in greater detail below.

The restriction devices may take on various shapes and be formed from any number of suitable materials, such as glass, ceramic, steel, and so forth. For example, in one particular embodiment, the restriction devices are opposed flat planar members disposed within the housing such that fluid from the inlet flows radially between the opposing surfaces. In one particular embodiment, fluid from the inlet is directed to the outer circumference of the restriction devices and flows radially inward between the opposing surfaces. The bottom (downstream) member has an orifice defined therethrough that defines an exit path for the fluid from between the planar members. The orifice is aligned with, or otherwise in fluid communication with, the housing outlet.

In an alternate embodiment, the upstream restriction device (e.g., an upstream flat planar member) may have an opening or orifice and the flow path within the housing is established such that fluid flows through this orifice and then migrates radially outward between the opposing surfaces prior to flowing to the outlet.

The flat planar member restriction devices may take on various shapes, sizes, thicknesses, etc. In one particular embodiment, the members are circular discs stamped or otherwise formed from a desired material. Such devices may be desired from the standpoint of ease of manufacture and assembly.

It should be appreciated that it is not necessary that each of the opposing surfaces is purposefully roughened as compared to the other. A desired relative degree of surface roughness along the restrictive flow path may be achieved by treating only one of the surfaces. The other surface may be untreated and relatively smooth. Alternately, the surfaces may have an inherent degree of surface roughness such that neither surface need be treated.

In an alternate embodiment, the restriction devices may be defined by a conical male member that mates within a complimentary shaped recess such that the opposing surfaces are defined by the conical wall of the male member and the recess wall. The conical member may have straight sides (i.e., constant slope) or curved sides. This embodiment may be desired in that a larger surface area between the opposing surfaces of the restriction devices may be achieved, thus permitting a greater degree of metering or fluid restriction.

In yet another embodiment, the restriction devices may be defined by a ball member seated within a ball seat such that the opposing surfaces are defined by a circumferential portion of the ball member and the ball seat. One or both of these surfaces may be roughened.

The restriction devices may be formed of a hard, non-compressible material, such as a medical grade stainless steel, so that fluid flow between the opposing surfaces is substantially constant regardless of a compressive pressure applied to restriction devices from fluid pressure or assembly of the housing components. In an alternate embodiment, the restriction devices may be formed of a compressible material, such as a medical grade polymer material, so that fluid flow between the opposing surfaces may be changed or adjusted by varying a compressive pressure applied to the restriction devices, for example by way of housing components that may be threadedly engaged.

In a particular embodiment, the housing comprises separate halves, with the restriction devices being placed within the halves prior to joining the halves to form the complete housing. The halves may be separable after being joined for access to the restriction devices. For example, the halves may be threaded onto each other, or otherwise releasably engaged. Alternatively, the halves may be permanently joined, for example by way of an adhesive, weld, and so forth.

The restriction devices may be variously oriented within the housing relative to the inlet and outlet. For example, in one embodiment, the devices are disposed such that a plane between the opposing surfaces is generally perpendicular to an axis of the inlet and outlet. In an alternate embodiment, the restriction devices are disposed such that the plane between the opposing surfaces is generally parallel to an axis of the inlet and outlet.

The invention also encompasses any manner of medical fluid delivery system that incorporates one or more of the unique fluid restriction devices as described herein.

The invention will be described in greater detail below by reference to particular embodiments shown in the referenced figures.

BRIEF DESCRIPTION OF THE FIGURES

FIG. 3A is a cross-sectional view of the flow restrictor of FIG. 2, particularly illustrating the flow path for a fluid through the device.

FIG. 3B is an enlarged view of the section of the circumference of the flow restriction devices indicated in FIG. 3A.

FIG. 3C is a side view of an embodiment of compressible flow restriction devices.

DETAILED DESCRIPTION

Reference will now be made in detail to examples of the invention, one or more embodiments of which are illustrated in the figures. Each example is provided by way of explanation of the invention, and not meant as a limitation of the invention. For example, features illustrated or described as part of one embodiment may be used with another embodiment to yield still a further embodiment. It is intended that these and other modifications and variations be included within the scope and spirit of the invention.

Figure 1A:
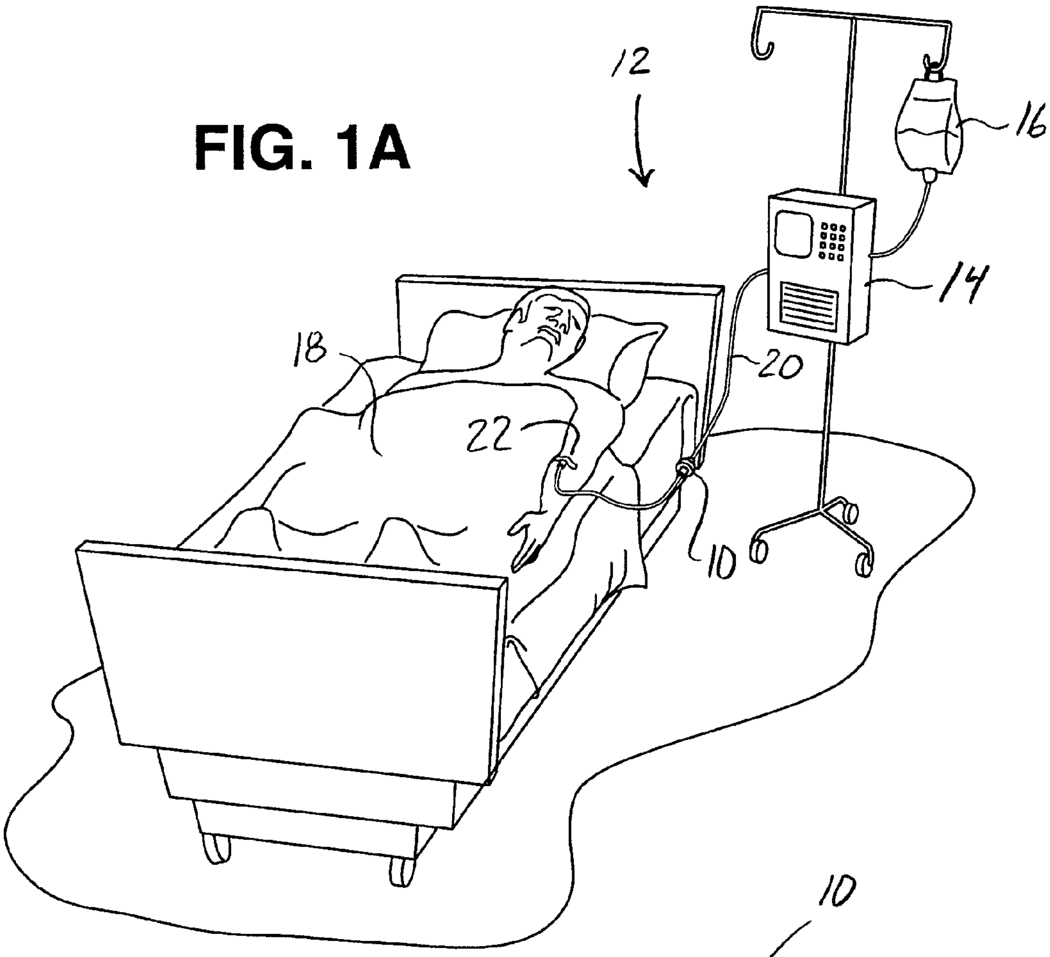
FIG. 1A is a perspective view of a conventional infusion pump system incorporating a flow restrictor according to the invention.

FIG. 1A illustrates an embodiment of a medical system, generally 12, that may utilize a flow restrictor 10 according to the invention. The medical system 12 is illustrated as a conventional infusion system wherein an infusion pump 14 is supplied with a fluid, such as a medicine, by a solution container 16 that is supported at a given height above the pump 14. Tubing 20 supplies the fluid from the pump 14 to an intravenous (IV) site 22 on a patient 18. Such infusion systems and pumps 14 are well known by those skilled in the medical art. Such systems are supplied, for example, by Braun Medical, Inc. of Bethlehem, Pa., and Baxter Healthcare Corporation of Round Lake, Ill. The flow restrictor 10 is illustrated as connected in-line in the tubing 20 between the pump 14 and the patient 18. It should also be appreciated that the restrictor 10 may be incorporated within the housing of the pump 14.

Figure 1B:
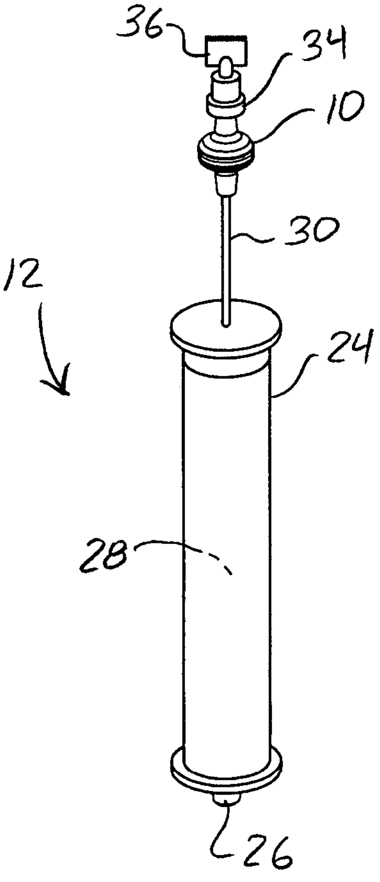
FIG. 1B is a perspective view of a conventional portable medical infusion system incorporating a flow restrictor according to the invention.
Figure 1C:
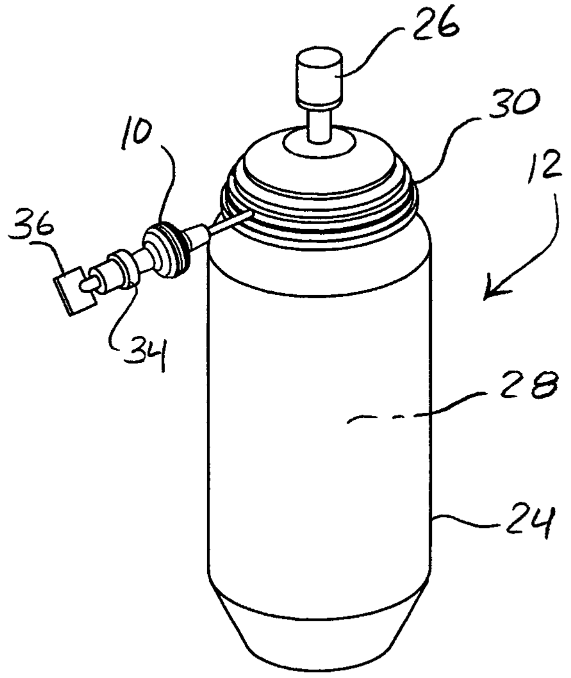
FIG. 1C is a perspective view of yet another conventional medical infusion system incorporating a flow restrictor according to the invention.

FIGS. 1B and 1C illustrate portable infusion systems that are generally worn or carried by a patient. Such devices are commercially available, for example, from Baxter Healthcare Corporation. FIG. 1B illustrates a small-volume system wherein a housing 24 defines an internal reservoir 28. A flexible membrane, such as an elastomeric balloon or the like, is contained within the reservoir 28 and provides fluid pressure. A fill port and associated cap 26 are provided for filling the reservoir 28. Delivery tubing 30 connects the housing 24 to a delivery end connector 34, such as a conventional luer connector. A cap 36 is provided for the connector 34. A flow restrictor 10 in accordance with the invention is provided in-line in the tubing 30 between the connector 34 and the housing 24. The connector 10 may be removably connected in the tubing 30, or permanently attached in the tubing 30, as described in greater detail below.

The infusion device of FIG. 1C is similar to that of FIG. 1B, but includes a larger housing 24 and internal reservoir 28. The reservoir 28 also includes an elastomeric "balloon" type of member for holding the fluid medication under sufficient pressure for delivery to the patient.

Although described with reference to infusion-type systems, it should be readily appreciated that the flow restrictor 10 according to the invention may be used in any medical system wherein it is desired to deliver a metered amount of a fluid to a patient from a pressurized source. For example, the restrictor 10 according to the invention can be utilized for continuous or intermittent delivery of fluids through clinically acceptable routes of administration, such as intravenous (IV), intra-arterial (IA), subcutaneous, epidural, or irrigation of fluid spaces applications.

Figure 2:
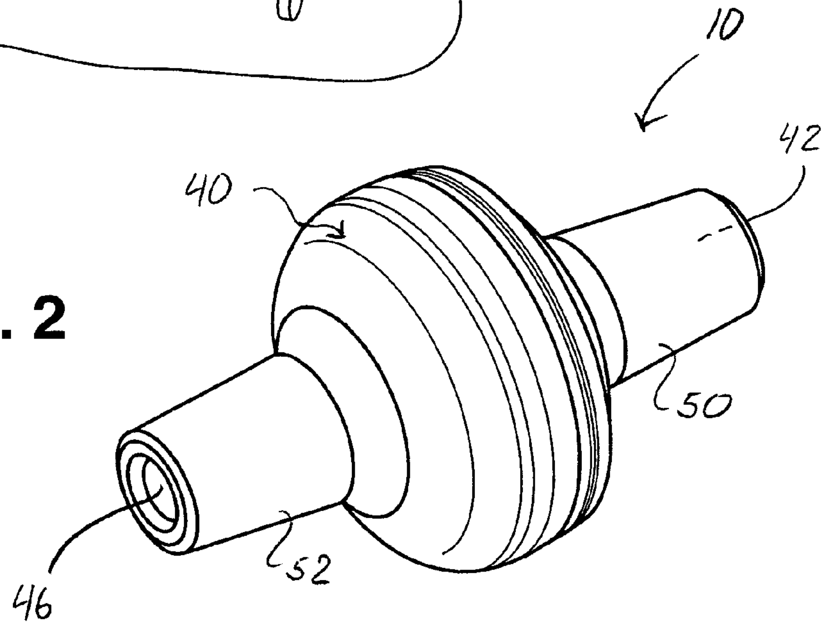
FIG. 2 is a perspective view of an embodiment of a flow restrictor according to the invention.

FIG. 2 illustrates an embodiment of the flow restrictor 10 in accordance with the invention. The restrictor 10 includes a housing 40 that may take on generally any desired shape or design. The housing 40, in one particular embodiment, is defined by separate halves or elements 50, 52, as described in greater detail below. The flow restrictor 10 includes an inlet 42 through which fluid is introduced into the device 10, and an outlet 46 from which fluid is conducted after flowing through the device 10.

Referring to FIGS. 3A through 3C, 4A, and 4B, the flow restrictor 10 of FIG. 2 is illustrated in greater detail. Housing 40 includes a first half 50 and a second half 52. The first half 50 defines the inlet 42 and an inlet passage 44. Similarly, the second half 52 defines an outlet passage 48 and the outlet 46. The halves 50, 52, may be configured to be releasably attached to medical tubing, for example by way of a clamp, or a simple friction or press fit of the tubing over the elongated ends of the respective halves 50, 52. Alternately, the tubing may be permanently attached to the respective halves 50, 52, by an adhesive, weld, or any other suitable permanent attachment means.

At least one pair of opposed restriction devices 60 are seated within the housing 40 between the inlet 42 and the outlet 46. The restriction devices 60 may take on various forms, so long as they define opposed surfaces placed in contact against each other such that a restrictive flow field 84 is defined between the opposed surfaces. For example, in the embodiment illustrated in the figures, the restriction devices 60 are defined by generally flat planar members **66*a* and 66*b* disposed against each other. The planar members may take on any shape, and in the figures are depicted as circular disks contained in the housing 40 by way of disk seats 58. Referring particularly to FIGS. 3A and 3B, it can be seen that at least one of the disks 66*a* or 66*b*, includes a generally "rough" surface such that when the opposing surfaces 62 and 64 are placed against each other, the restrictive fluid flow field 84 is defined between the surfaces. In the illustrated embodiment, each of the disks includes a roughened surface, as particularly seen in FIG. 3B. In this manner, there exists void spaces or valleys 72 and protrusions 70 that define a completely random restrictive flow field 84. It should be appreciated that the degree of surface roughness between the opposing surfaces 62, 64**, is grossly exaggerated in the figures for purposes of illustration only. It may very well be that, for many embodiments, the surface roughness is not discernible by the unaided eye.

By carefully controlling the degree of surface roughness of the opposed surfaces 62, 64, the rate of fluid flow between the matrix of valleys 72 and protrusions 70 along the field 84 may be controlled, and a relatively precise metering mechanism is defined. For a specific fluid pressure, a desired fluid flow rate can be achieved by carefully defining the particular parameters of surface roughness of each of the surfaces 62, 64, the surface area of contact between the surfaces 62, 64, and the pressure applied to the surfaces 62, 64. Taking these factors into consideration, the restriction devices **66*a* and 66*b* may be designed for a particular flow rate based on prediction algorithms. Alternatively, the dimensions and surface roughness of the devices 66*a*, 66*b***, may be empirically determined through routine experimentation.

The cylindrical disk-type restriction devices **66*a*, 66*b*, may be desired in that they are relatively inexpensive and easy to fabricate. For example, the components may be punched, stamped, turned, and so forth. Also, the desired degree of surface roughness of the disks 66*a*, 66*b***, may be achieved with conventional processes such as etching, sandblasting, lapping, grinding, tumbling, and so forth.

In the embodiment illustrated in FIGS. 3A and 3B, the restriction devices **66*a*, 66*b*, are formed from a relatively incompressible, hard material, such as stainless steel, glass, ceramic, and so forth. In this manner, the restrictive flow path 84 is predominantly unchanged or unaltered by the degree of compression of the devices against each other. Alternatively, it may be desired that the devices 66*a*, and 66*b*, are formed from a compressible material, such as a relatively soft poly material. In this manner, the restrictive field 84 may be made more or less restrictive depending upon the degree of compression of the components 66*a*, 66*b*, against each other, as is diagrammatically illustrated in FIG. 3C. The "soft" disks 66*a*, 66*b*, may be used in an embodiment wherein the housing halves 50, 52, are relatively adjustable relative to each other, for example as in a threaded engagement between the two halves. With this configuration, different flow rates may be achieved with a single restrictor 10**, or the restrictor may be adjusted or fine-tuned for achieving a very accurate flow rate.

Figure 4A:
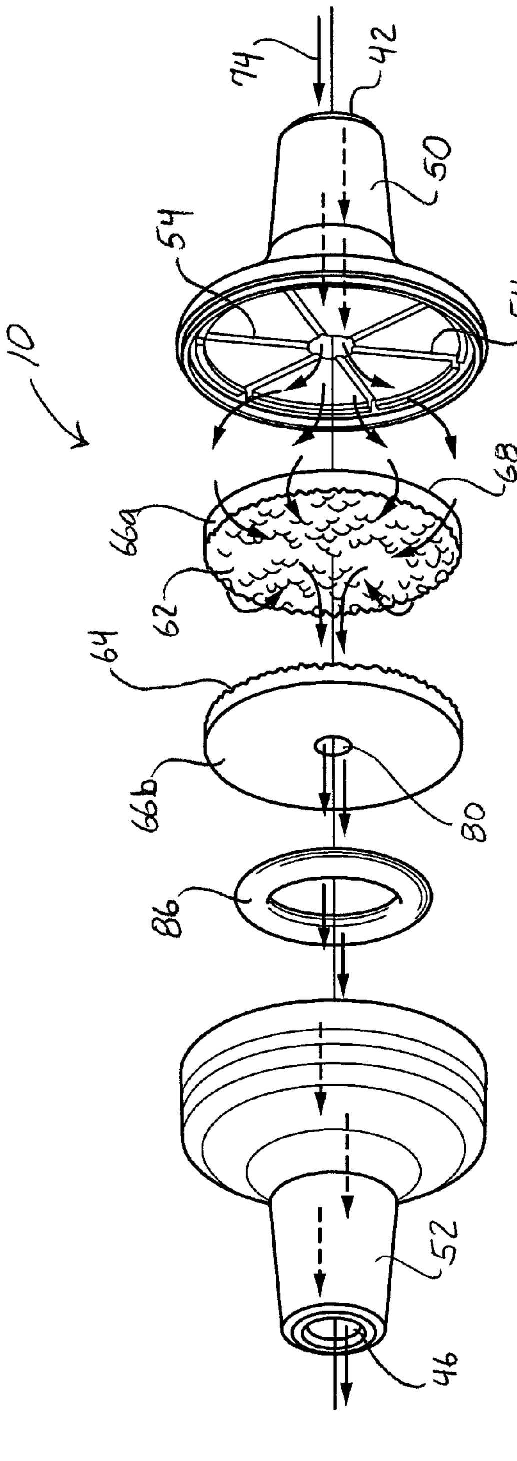
FIG. 4A is an in-line component view of an embodiment of the flow restrictor particularly illustrating the fluid flow path from the inlet to the outlet.
Figure 4B:
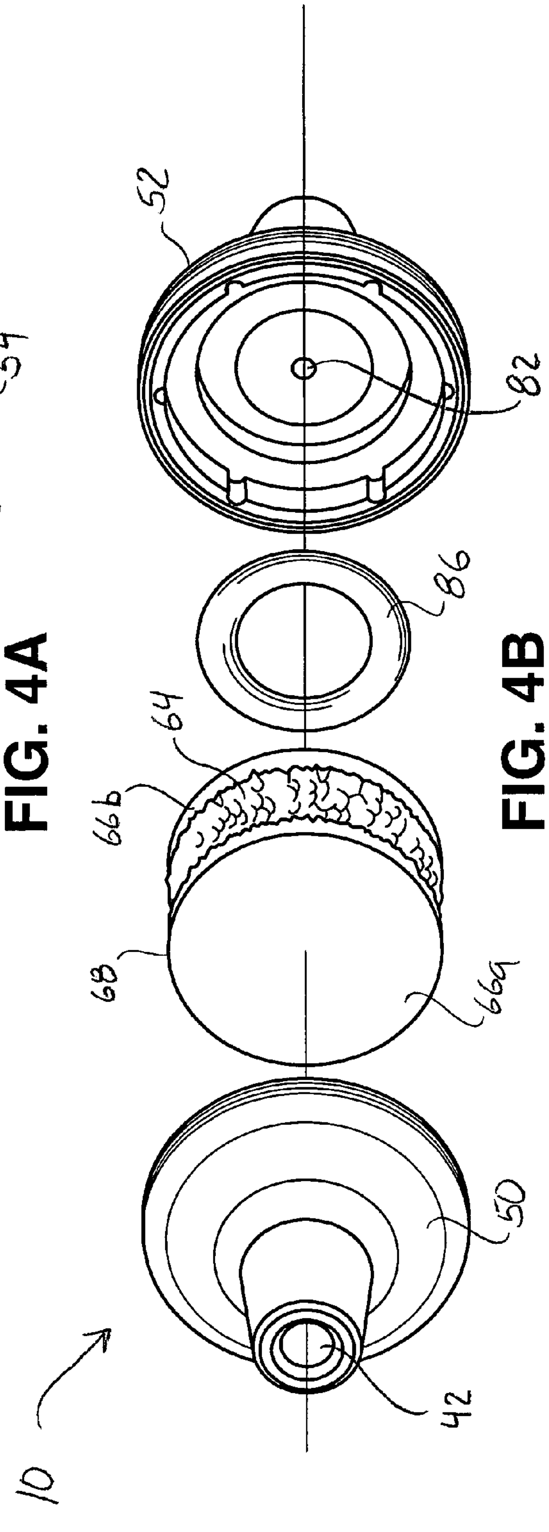
FIG. 4B is an in-line component view of the embodiment of FIG. 4A taken from the opposite direction.

FIGS. 3A and 4A illustrate the flow path 74 of a fluid through one embodiment of the restrictor 10. In this particular embodiment, the fluid moves under pressure through the inlet 42 and inlet passage 44 and is directed to the perimeter or circumference 68 of the restriction devices **66*a*, 66*b*, by way of relief channels 54 or other suitable structure defined in the housing half 50. A sealing device 86, such as a conventional O-ring, gasket, or any other suitable elastomeric sealing device, is disposed in a seat 56 in the housing second half 52, as particularly seen in FIG. 3A. This seal 86 prevents the fluid from bypassing the restrictive field 84. Referring particularly to FIG. 3A, it can be seen that the fluid migrates from the circumference of the restriction devices 66*a*, 66*b* radially inward at a rate that is defined as a function of the surface roughness and surface area of the opposed surfaces 62, 64, of the restriction devices, as discussed above. The fluid migrates to an orifice 80 defined in the downstream restriction device 66*b*. The orifice 80 is in fluid communication with the outlet passage 48, for example by way of an orifice passage 82**.

It should be appreciated that any number of configurations of internal structure, sealing devices, and so forth, may be utilized within a housing 40 to ensure that fluid is directed through the restrictive field 84 of opposed restriction devices **66*a*, 66*b* to disburse the fluid from the outlet 46 at a desired flow rate. It may be desired to incorporate the sealing element in the housing, for example by way of a two-shot injection molding process wherein the second shot is an elastomer. Alternatively, a sealing element may be provided on one or both of the disks 66*a*, 66*b* (or other type of restriction devices). For example, the disks 66*a*, 66*b*** may be stamped from a composite metal/rubber sheet wherein the metal component defines an opposing surface of the restriction device, and the rubber component defines the seal. In still an alternative embodiment, the seal need not be elastomeric. For example, the seal may be defined by an epoxy, glue, or ultrasonic bond between the disk and a housing member.

Thus far, the restrictor 10 according to the invention has been described with opposed roughened surfaces 62, 64. However, it should be appreciated that the invention also includes the configuration wherein only one of the surfaces 62, 64, is roughened. In other words, the restrictive flow field 84 may be achieved by opposed surfaces wherein one of the surfaces is relatively smooth or polished with respect to the other surface. Alternatively, for ease of manufacturing, assembly, and so forth, it may be desired that all of the components are essentially the same and axis-symmetric. For example, if both sides of the restriction disk 66*a*, 66*b* are treated (rough), then assembly is facilitated by eliminating a particular surface to surface orientation. This design is optimized for pick-and-place automated assembly.

It should also be appreciated that, for varying flow rates, several restrictive devices may be stacked within a common housing.

The halves of the housing 40 may be releasably attached to each other after insertion of the sealing device 86 and restriction devices 66*a*, 66*b*, or permanently attached to each other. For example, the halves, 50, 52, may be threadedly engaged such that the device 10 may be subsequently taken apart for replacement of the restriction devices 66*a*, 66*b*. In an alternative embodiment, the halves 50, 52 may be permanently adhered to each other with an adhesive, ultrasonic bonding, welding, or any other conventional attaching means.

Figure 5:
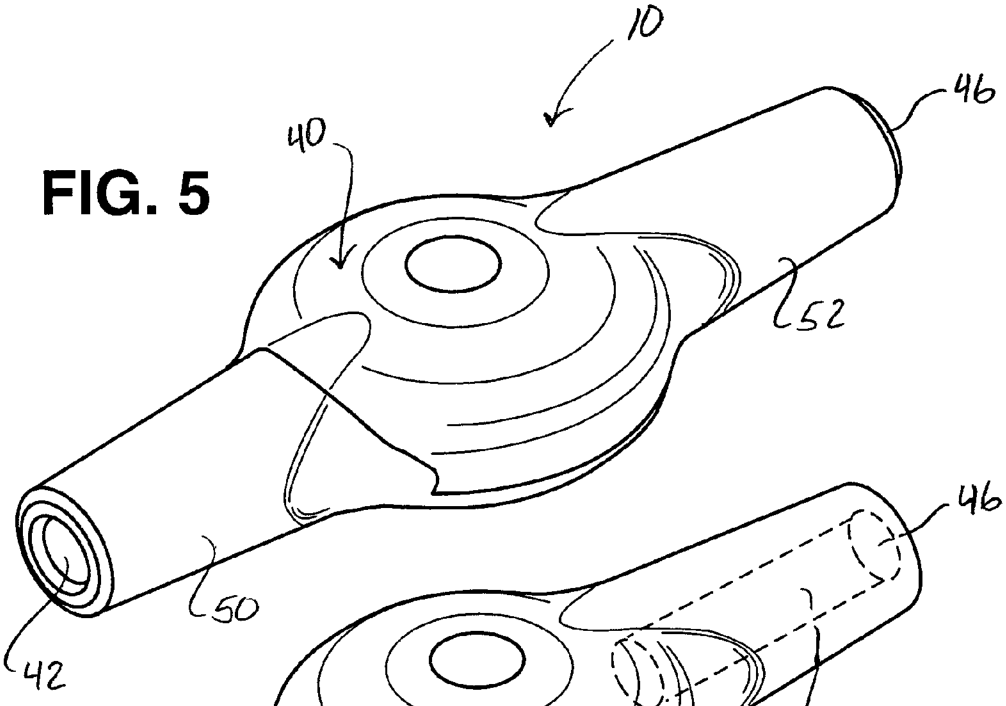
FIG. 5 is a perspective view of an alternate embodiment of a flow restrictor according to the invention.
Figure 6:
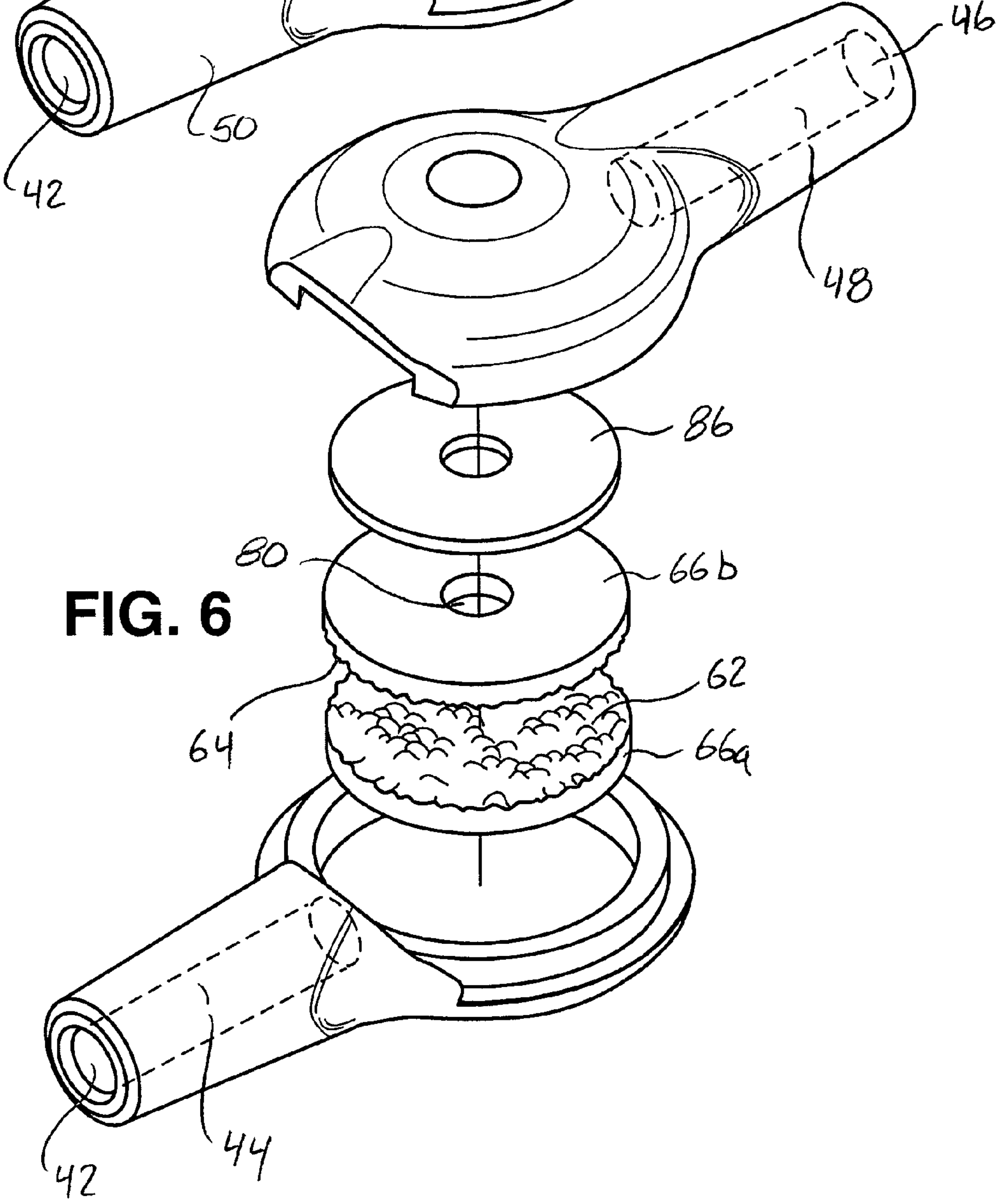
FIG. 6 is a component view of the embodiment of FIG. 5.

It should also be appreciated that the restriction devices 66*a*, 66*b*, may be variously oriented within the housing 40. For example, in the embodiment illustrated in FIGS. 3A, 4A, and 4B, the devices 66*a* and 66*b* are oriented such that a plane between the opposing surfaces 62, 64, is generally perpendicular to the axis of the inlet and outlet of the housing 40. FIGS. 5 and 6 illustrate an alternative embodiment wherein the restriction devices 66*a*, 66*b*, and seal 86 (gasket) are oriented within the housing 40 such that the plane between the restriction devices is generally parallel to the axis of the inlet and outlet of the housing 40. Regardless of the orientation of the restriction devices 66*a*, 66*b*, the operation of the device is essentially as described above with reference to the embodiment of FIGS. 3A and 4A, and 4B.

Figure 7:
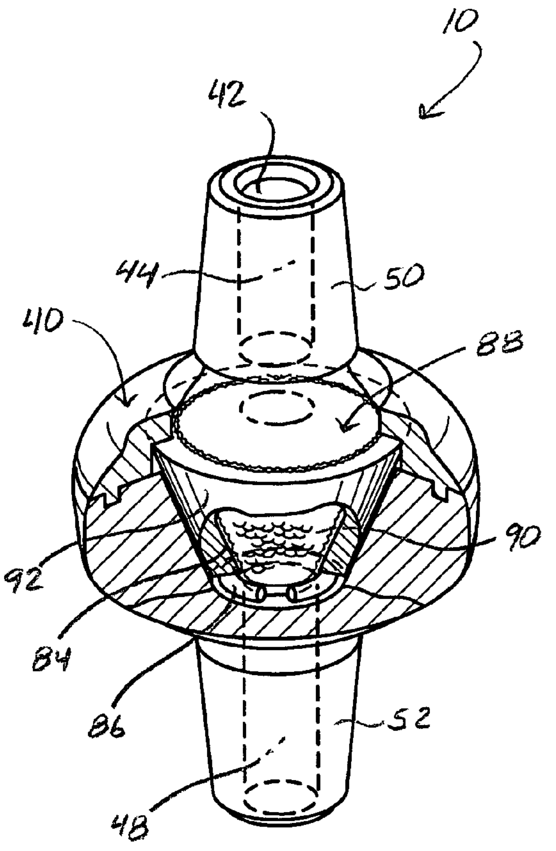
FIG. 7 is a perspective and partial cut-away view of an alternative embodiment of a flow restrictor according to the invention utilizing conical restriction devices.
Figure 8:
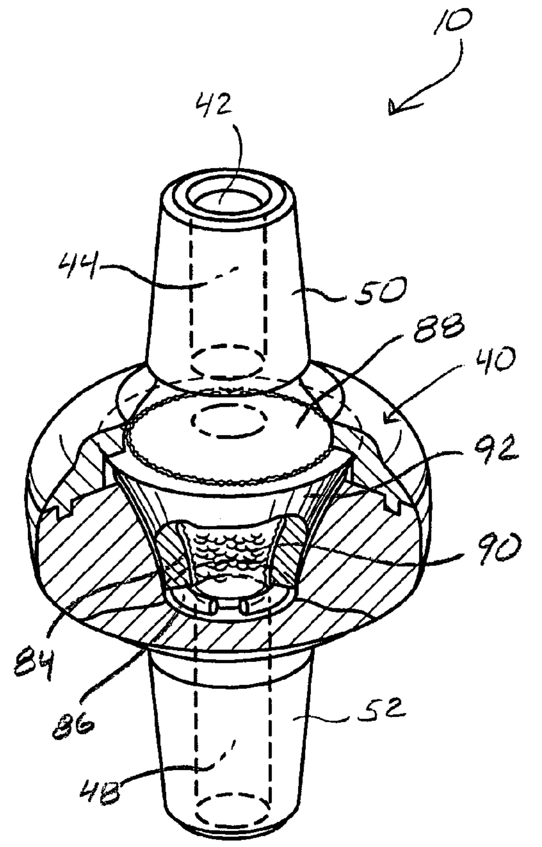
FIG. 8 is a perspective and partial cut-away view of an alternative embodiment of a flow restrictor according to the invention utilizing conical restriction devices having radially curved side walls.

It should also be appreciated that the restriction devices 60 may take on various shapes and configurations. For example, in the embodiments of FIGS. 7 and 8, conical restriction devices 88 are provided. A conical or truncated male member 90 having a rough outer surface is seated within a correspondingly shaped recess of an opposite member 92. The restrictive flow path is thus defined between the conical walls of the members 90 and 92, wherein at least one of these opposed surfaces defines a roughened surface. In the embodiment of FIG. 7, the conical opposed surfaces are relatively straight in that they have a constant slope. In the embodiment of FIG. 8, the opposed conical surfaces are curved, or have a radial component along at least a portion thereof. The embodiments of FIGS. 7 and 8 provide for an increased surface area between the opposed surfaces defining the restrictive flow field 84, as compared to the flat disk devices 66*a*, 66*b*, of the prior embodiments.

Figure 11:
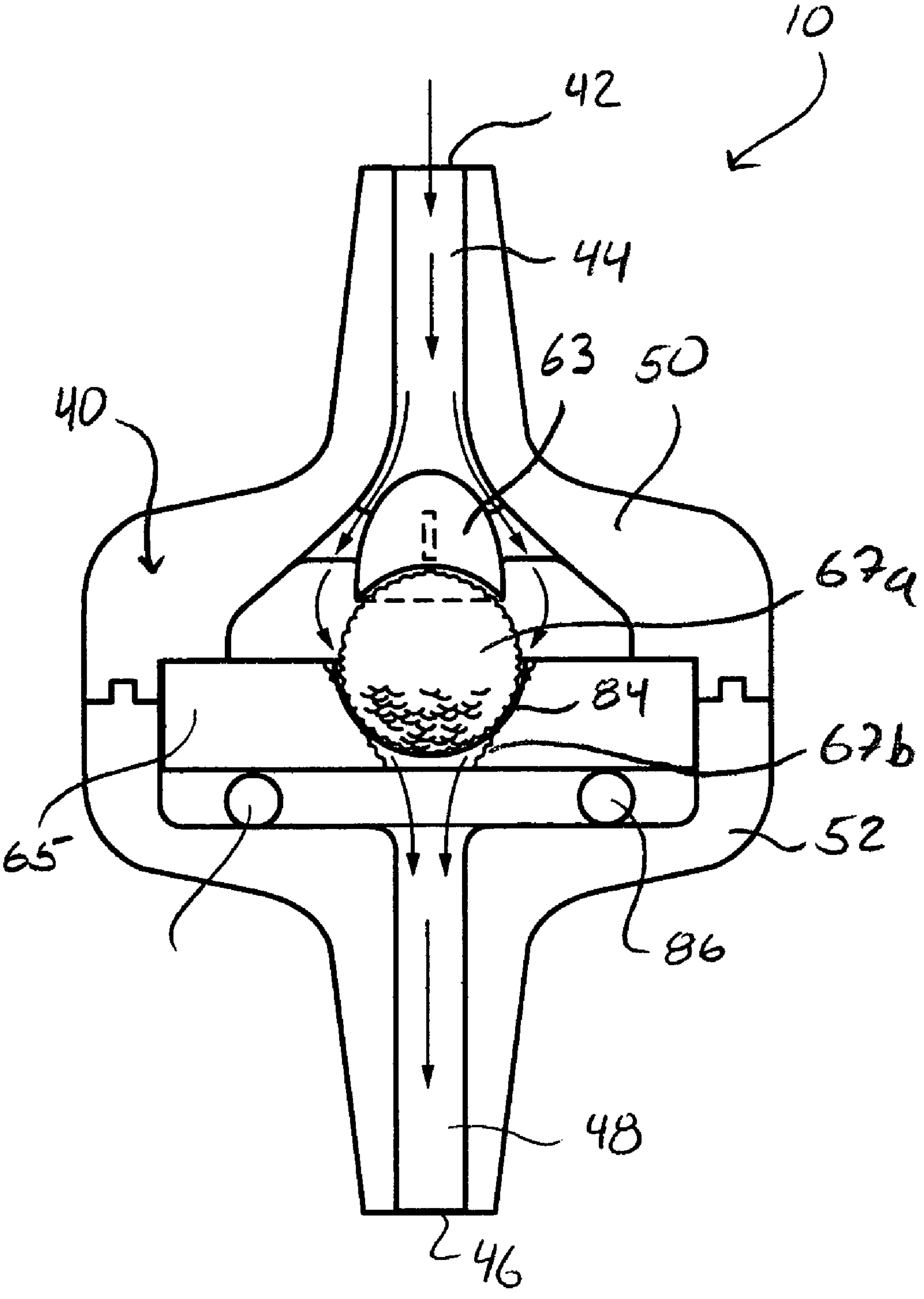
FIG. 11 is a cross-sectional diagrammatic view of an embodiment of a flow restrictor wherein the restriction devices include a ball seated within a ball seat.

FIG. 11 illustrates an embodiment of a flow restrictor 10 wherein the restriction devices are defined by a ball member 67*a* and a planar member 65 having a ball seat 67*b* defined therein. The restrictive fluid flow path 84 is defined between the circumferential portion of the ball member 67*a* and surface of the ball seat 67*b*. Either one or both of the ball surface or ball seat may be roughened. A flow distributor 63 may be incorporated within the housing as an integrally formed or separate component. The distributor 63 may take on any shape to direct fluid from the inlet passage 44 to the restrictive fluid flow path 84 and may also serve to positively engage and contain the ball 67*a* within the ball seat 67*b*. This embodiment may be desired from the standpoint of cost and ease of manufacture.

It should be appreciated that various configurations of restrictive devices may be derived empirically or otherwise by those skilled in the art to define a restrictive flow field between opposed surfaces in accordance with the principles of the present invention.

Figure 9:
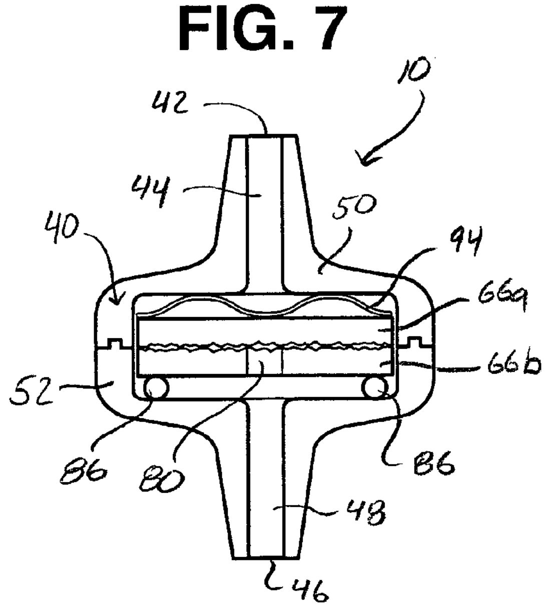
FIG. 9 is a cross-sectional diagrammatic view of an alternate embodiment of a flow restrictor incorporating a biasing element with the housing.

FIG. 9 illustrates an embodiment of a restrictor 10 incorporating a resilient biasing element within the housing 40. The biasing element may be in the form of a wave spring 94 as illustrated in the FIG. 9, or may be any other conventional biasing element such as a spring, and so forth. The biasing element serves to ensure that the restriction devices 66*a*, 66*b* are biased together so that the opposing surfaces properly define the desired restrictive flow path. It should also be appreciated that the sealing element 86 in the embodiments of FIG. 3*a* and FIG. 11, for example, may be formed of an elastomeric material and may also serve the function of biasing the restriction devices together.

Figure 10:
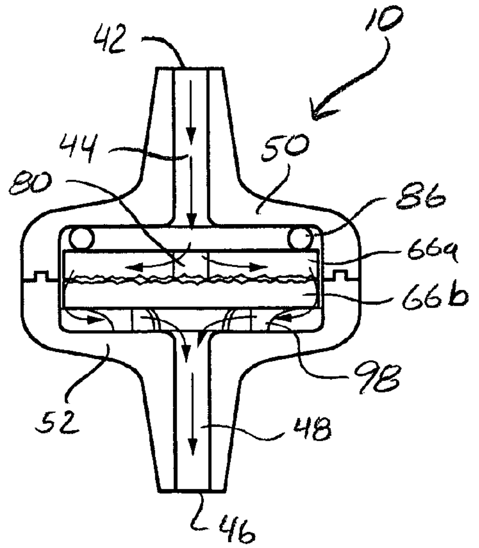
FIG. 10 is a cross-sectional diagrammatic view of an embodiment of a flow restrictor having a flow path such that fluid flows radially outward between the opposed surfaces of the restriction devices.

FIG. 10 is an embodiment of a restrictor 10 wherein the fluid flows in a radially outward direction along the restrictive flow path between the restriction devices 66*a*, 66*b*. An orifice 80 is defined generally at the center of the upstream restriction device 66*a*. The sealing device (ring) 86 is disposed concentric about the orifice 80 such that fluid entering from inlet passage 44 is caused to flow through the orifice 80 to the restrictive flow path defined by the opposing surfaces of the restriction devices 66*a*, 66*b*. The fluid then flows radially outward along the flow path, as indicated by the arrows in FIG. 10, and around the periphery of the downstream restriction device 66*b* where it is directed to the outlet passage 48. Ridges 98, or any other suitable support structure, are provided within the housing to support the restriction device 66*b* and define a flow path for the fluid to the outlet passage 48.

It should be appreciated by those skilled in the art that modifications and variations may be made to the embodiments described above without departing from the scope and spirit of the invention. It is intended that the invention include these and other modifications as come within the scope and spirit of the appended claims and their equivalents.

What is claimed is:

1. A medical apparatus flow restrictor, comprising:

a housing having an inlet and an outlet, and a fluid path defined through said housing between said inlet and said outlet;

at least one pair of opposed restriction devices seated within said housing between said inlet and said outlet, said restriction devices comprising opposing planar surfaces placed in contact against each other in an axial direction, a first one of said surfaces being carried on a first continuous rigid restriction device, the second one of said surfaces being carried on a second rigid restriction device that is continuous except for at least one opening therethrough, said opening being disposed in communication with said inlet and said outlet, said restriction devices defining outermost peripheral edges, said restriction surfaces disposed in said flow path such that fluid delivered to said inlet always passes between said opposing surfaces via said outermost peripheral edges of said restriction devices and said opening of said second continuous restriction device prior to flowing from said outlet; and wherein said opposing surfaces have a random surface roughness and opposed surface area defining a random flow field between said opposed surfaces, the degree of said random surface roughness and surface area of said random flow field defined as a function of a desired flow rate of fluid through said restrictor, and wherein said random flow field is defined by a random pattern of voids, spaces, valleys and protrusions between said opposing planar surfaces and defines the sole regulated restrictive flow path through said restrictor for delivering a desired flow rate.

2. The restrictor as in claim 1, wherein said restriction devices comprise opposed flat circular planar members disposed within said housing such that fluid from said inlet flows radially between said opposing surfaces of said flat planar members.

3. The restrictor as in claim 2, wherein a flow path is defined within said housing such that the fluid flows to a perimeter of said flat planar members and migrates radially inward between said opposing surfaces of said flat planar members.

4. The restrictor as in claim 1, wherein said restriction devices are formed of a hard, con-compressible material such that fluid flow between said opposing surfaces is substantially constant regardless of a compressive pressure applied to said restriction devices.

5. The restrictor as in claim 1, wherein said housing comprises separate halves, said restriction devices placed within said halves prior to joining said halves to form said housing.

6. The restrictor as in claim 5, wherein said halves are separable after being joined for access to said restriction devices.

7. The restrictor as in claim 5, wherein said halves are permanently and non-separably joined.

8. The restrictor as in claim 1, further comprising a seal disposed within said housing relative to said restriction devices to ensure that fluid flow through said restrictor does not bypass said fluid flow path between said opposing surfaces.

9. The restrictor as in claim 1, wherein said restriction devices are disposed such that a plane between said opposing surfaces is generally perpendicular to an axis of said inlet and said outlet.

10. The restrictor as in claim 1, wherein said inlet and said outlet are connectable to tubing in fluid delivery system such that said restrictor is placeable in-line within said system.

11. The restrictor as in claim 1, wherein said opposing surfaces are disposed in a generally flat plane essentially perpendicular to an axis of said inlet and said outlet.

12. The restrictor as in claim 1, wherein said surface roughness of at least one of said opposing surfaces is defined in any one or combination of a controlled grinding, lapping, tumbling, sandblasting, or etching process.

13. The restrictor as in claim 1, wherein each of said opposing surfaces is roughened.

14. The restrictor as in claim 1, wherein only one of said opposing surfaces is roughened as compared to said other opposing surface.

15. The restrictor as in claim 1, further comprising a biasing element disposed within said housing so as to bias said restriction devices together.

16. A medical apparatus flow restrictor, comprising:

a housing having an inlet and an outlet, and a fluid path defined through said housing between said inlet and said outlet;

at least one pair of opposed restriction devices seated within said housing between said inlet and said outlet, said restriction devices comprising opposing planar surfaces placed in contact against each other in an axial direction, a first one of said surfaces being carried on a first continuous rigid restriction device, the second one of said surfaces being carried on a second rigid restriction device that is continuous except for at least one opening therethrough, said opening being disposed in communication with said inlet and said outlet, said restriction devices defining outermost peripheral edges, said restriction surfaces disposed in said flow path such that fluid delivered to said inlet always passes between said opposing surfaces via said outermost peripheral edges of said restriction devices and said opening of said second continuous restriction device prior to flowing from said outlet;

wherein said opposing surfaces have a relative degree of surface roughness and opposed surface area defining a random flow field as a function of a desired flow rate of fluid through said restrictor, and wherein said random flow field is defined by a random pattern of voids, spaces, valleys and protrusions between said planar opposing surfaces and defines the sole regulated flow path through said restrictor; and wherein said restriction devices are formed of a compressible material such that fluid flow between said opposing surfaces is varied by varying a compressive pressure applied to said restriction devices.

17. A medical fluid delivery system configured to deliver a fluid from a source to a patient at a regulated flow rate, said system comprising delivery tubing and a flow restrictor placed in-line in said tubing, said flow restrictor further comprising:

a housing having an inlet and an outlet, and a fluid path defined through said housing between said inlet and said outlet;

at least one pair of opposed restriction devices seated within said housing between said inlet and said outlet, said restriction devices comprising opposing planar surfaces placed in contact against each other in an axial direction, a first one of said surfaces being carried on a first continuous rigid restriction device, the second one of said surfaces being carried on a second rigid restriction device that is continuous except for at least one opening therethrough, said opening being disposed in communication with said inlet and said outlet, said restriction devices defining outermost peripheral edges, said restriction surfaces disposed in said flow path such that fluid delivered to said inlet always passes between said opposing surfaces via said outermost peripheral edges of said restriction devices and said opening of said second continuous restriction device prior to flowing from said outlet; and wherein said opposing surfaces have a random surface roughness and opposed surface area defining a random flow field between said opposed surfaces, the degree of said random surface roughness and surface area of said random flow field defined as a function of a desired flow rate of fluid through said restrictor, and wherein said random flow field is defined by a random pattern of voids, spaces, valleys and protrusions between said planar opposing surfaces and defines the sole regulated flow path through said restrictor.

18. The fluid delivery system as in claim 17, wherein said flow restrictor is disconnectable from said tubing.

19. The fluid delivery system as in claim 17, wherein said restriction devices comprise opposed flat circular planar members disposed within said housing such that fluid from said inlet flows from a perimeter of said flat planar members and migrates radially inward between said opposing surfaces of said flat planar members.

20. The fluid delivery system as in claim 17, wherein said housing comprises separate halves, said restriction devices placed within said halves prior to joining said halves to form said housing.

21. The fluid delivery system as in claim 17, further comprising a seal disposed within said housing relative to said restriction devices to ensure that fluid flow through said restrictor does not bypass said fluid flow path between said opposing surfaces.

22. The fluid delivery system as in claim 17, wherein said restriction devices are disposed such that a plane between said opposing surfaces is generally perpendicular to an axis of said inlet and said outlet.

* * * * *